United States Patent [19]

Ohashi et al.

[11] Patent Number: 4,579,880
[45] Date of Patent: Apr. 1, 1986

[54] DENTAL CAVITY FILLING COMPOSITE MATERIAL

[75] Inventors: Masayoshi Ohashi; Misaki Anzai, both of Tokyo, Japan

[73] Assignee: Nihon University, Tokyo, Japan

[21] Appl. No.: 603,648

[22] Filed: Apr. 24, 1984

[30] Foreign Application Priority Data

Aug. 11, 1983 [JP] Japan .................. 58-147690

[51] Int. Cl.$^4$ .............................. A61K 6/08
[52] U.S. Cl. ................ 523/116; 260/998.11; 433/228.1; 523/117; 526/276; 528/399
[58] Field of Search .......... 433/226, 228; 526/276; 260/543 PN, 998.11; 528/399, 168; 523/116, 117

[56] References Cited

U.S. PATENT DOCUMENTS

| | | | |
|---|---|---|---|
| 3,311,622 | 3/1967 | Joffre | 260/543 PN |
| 4,061,606 | 12/1977 | Dieck et al. | 528/168 |
| 4,200,721 | 4/1980 | Fletcher | 526/276 |
| 4,242,491 | 12/1980 | Hergenrother et al. | 528/399 |
| 4,321,217 | 3/1982 | Allcock et al. | 526/276 |

*Primary Examiner*—Lorenzo B. Hayes
*Attorney, Agent, or Firm*—Browdy and Neimark

[57] ABSTRACT

A dental filling composite material is disclosed, which contains 10–99% by weight of phosphazene of the formula:

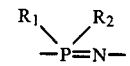

in which at least one of $R_1$ and $R_2$ represent radicals having not less than 3 carbon atoms and being polymerizable.

The filling composite material is low in polymerization shrinkage, thermal expansion coefficient and water absorption and may be quickly polymerized and cured to form a polymer of high compressive strength, flexural strength and hardness.

4 Claims, No Drawings

DENTAL CAVITY FILLING COMPOSITE MATERIAL

FIELD OF THE INVENTION

This invention relates to a filling composite material having highly improved mechanical properties, and being very low in polymerization shrinkage, thermal expansion coefficient and water absorption. More particularly, it relates to a dental filling composite material which is easy to be filled into loss cavities of front teeth and molars, quick to be polymerized, low in polymerization shrinkage, thermal expansion coefficient and water absorption and may be readily polymerized and cured to form a polymer of high compressive strength, flexural strength and hardness.

BACKGROUND OF THE INVENTION

Materials such as amalgam and silicate cement have hitherto been used as dental filling materials. These materials, however, have no adhessiveness to tooth substance but have liability to cause secondary caries. Further, some uncertainty with regard to durability and fear of injuriousness to the pulp or soft tissues have compelled these materials to be replaced by resin type filling materials. In other words, a monomer to be used as the dental filling material is a mixture of polymethyl methacrylate and metyl methacrylate, of bisphenol-A glycidyl dimethacrylate and ethyleneglycol dimethacrylate, or of urethane dimethacrylate, 2,2-di-(4-methacryloxy ethoxy phenol)propane and triethylene glycol dimethacrylate. Such mixture is incorporated with fillers such as silica power and amines such as dimethyl-p-toluidine and p-tolyldiethanolamine, as well as peroxides such benzoyl peroxide. Then, the resulting mixture is polymerized by amine-peroxide system to form the filling materials.

As well-known in the art, however, such monomer has a C—C homo bond in its chain and skeleton and therefore produces a polymer of high flexibility and bending, but has disadvantages of high thermal expansion coefficient and low heat-resistance. In other words, the resulting polymer is low in strength and hardness, large in polymerization shrinkage and low in softening point. Consequently, if the above-mentioned mixture of monomers is filled into dental cavities, gaps may be produced between cavities and polymers due to polymerization shrinkage and temperature change upon eating and drinking, thereby to cause secondary caries. In addition, the polymer has poor hardness and strength, resulting in ready wearability and poor durability.

SUMMARY OF THE INVENTION

A general object of the invention is to completely solve the problems as described hereinabove and to provide an improved dental filling composite material which is not injurous to the pulp and the soft tissues and forms an eternal prosthesis.

A principal object of the invention is to provide a filling compostie material containing 10 to 99% by weight of phosphazene of the formula:

in which at least one of $R_1$ and $R_2$ represents radicals having not less than 3 carbon atoms and being polymerizable.

PREFERRED EMBODIMENT OF THE INVENTION

In accordance with the invention any phosphazene of the formula:

in which $R_1$ and $R_2$ are defined hereinabove, may be used but it is preferred to select the following phosphazene:

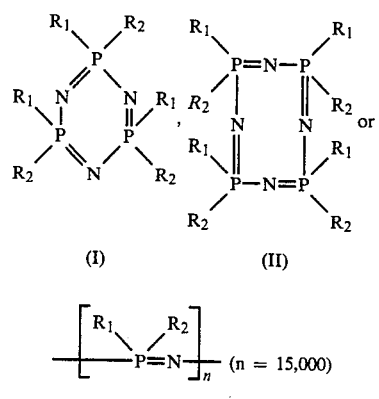

In the above formulae, at least one of the radicals $R_1$ and $R_2$ has not less than 3 carbon atoms and polymerizable groups. As the polymerizable groups, there may be mentioned those compounds that can be polymerized by polycondensation, addition polymerization and by ring-opening polymerization, especially those compounds having vinyl groups that can be polymerized by radical polymerization. Further, it has been found that those compound whose $R_1$ or $R_2$ has 1-3—$NH_2$ groups show adhessiveness, while those having 1-3 phenol groups show highly improved heat-resistance.

Compounds having

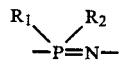

bonds are, as is generally known, of hetero bond which has a higher bonding energy than that of homo bond, and inhibits molecular rotation. Thus, the compounds show inorganic properties, such as low flexural strength, high hardness, poor flexibility and high decomposition point and hence are called inorganic oligomers or inorganic high polymers.

It will be apparent from the foregoing that polymers of the compounds according to the present invention have highly improved mechanical properties, and other preferable properties such as polymerization shrinkage and thermal expansion coefficient, as well as excellent durability and practical usefulness and thus show excellent properties as dental filling composite materials.

The invention may be embodied by reaction of organic compounds having vinyl groups with phosphazene as described hereinabove, or by polymerization of monomers having vinyl groups or copolymerization of monomers having vinyl groups with other monomers.

As copolymerizable monomers to be used in the invention, there may be mentioned acrylic acid, methacrylic acid and their esters, especially hydroxy alkyl ester and sodium salt of alkyl ester, more preferably hydroxy ethyl acrylate, hydroxy ethyl methacrylate and hydroxy propyl methacrylate.

In general, the compounds having the radical

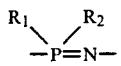

may be synthesized in the following way.

In either case of trimer or tetramer of phosphonitrilic chloride, chlorine atom bonded to phosphorus is substituted by other atom or atomic group in a solvent such as dioxane, benzene or tetrahydrofuran.

Alternatively, the trimer of phosphonitrilic chloride(-hexachloro-cyclo-triphosphazene) may be heated in a sealed tube for about 20 hours at 250° C. to form the compound of the formula:

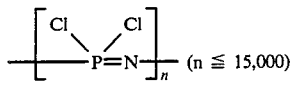

which in turn is substituted for its substituents in the similar way as described hereinbefore. When the compound having vinyl groups as the polymerizable groups is reacted, benzene is preferably used as a solvent.

In order to polymerize phosphazene having vinyl groups at an ambient temperature, there may be used an amine-peroxide type of polymerization initiator. Upon polymerization under ultra-violet radiation or visible light, there may be practically and clinically used a dibenzoyl or benzoin methyl ether-amine type of initiator.

Alternatively, the phosphazene compound having the vinyl groups according to the invention may be combined with 5-90 parts by weight of monomethacrylate and polyfunctional monomers, that is, copolymerizable monomers such as triethylene glycol dimethacrylate, bisphenol-A diglicidyl dimethacrylate, trimethylolpropane trimethacrylate and tetramethylol methane tetraacrylate and then cured in the similar way as described hereinabove.

On the other hand, the physical properties of the cured product may be improved by incorporating 40-85 parts by weight of at least one type of powder selected from silica, alumina, barium silicate, colloidal silica, white carbon and silicon carbide of less than 10 μm into the phosphazene compound alone or into a composition thereof with the copolymerizable monomers as described hereinabove.

Two packages are required in the self-curing process, one of which in the form of a paste or solution is incorporated with peroxide while the other in the form of a paste or powder with an amine type of accelerator. The former package may be mixed with the latter and then cured for 2-3 minutes, which may be used clinically in the same way as of the conventional composite resin, namely it may be bonded by any conventional bonding agent, and then filled and polished.

In the light-curing process, on the other hand, single package should be used. The above-mentioned composition may be mixed with dibenzoyl and trihexyl amine together with inhibitor to form a paste, which is filled into the loss cavity of tooth in 4 mm thickness and irradiated with 350-550 nm light for about 20 seconds in the conventional method for curing.

Thus, the filling composite material containing the phosphazene compound according to the invention may be used in the conventional method, irrespective of the polymerization procedure, for obtaining more improved mechanical and other physical properties than could be reached by the conventional method, thereby to achieve the remarkable effect of providing the long-lasting or eternal filling material.

The invention will be described hereinbelow by means of the non-limiting examples.

EXAMPLE 1

A phosphazane compound was synthesized and polymerized to form a dental filling composite material in the following way:

(1) Synthesis of 1,1,3,3,5,5-hexa-(methacryloyl ethylenedioxy)-cyclotriphosphazene 52.2 g of hexachloro cyclo triphosphazene together with 300 ml of anhydrous benzene was put into a 2 l three-neck flask and cooled with ice, to which 175.7 g of refined hydroxyl ethyl methacrylate was added. Then, 142.3 g of pyridine was added dropwise through a filter funnel with stirring for about 3 hours. The mixture was stirred for 60 hours at 80° C. an ice-cooled to filter off pyridine hydrochloride, and after being washed with 120 ml of 2N hydrochloric acid 3 times, then with 200 ml of 5% sodium chloride solution twice to remove excessive pyridine, was dehydrated by about 40 g of anhydrous magnesium sulfate. Then, benzene was removed under the reduced pressure to give a syrup, which in turn was washed with 150 ml of hexane and then with 200 ml of petroleum ether to remove unreacted monomers to obtain 120.6 g of clear oil.

The product is soluble in benzene, acetone and ethanol, but insoluble in water, diethyl ether, xylene and hexane. Its decomposition point is in the range of 280° C.-780° C.

(2) Polymerization procedure 99.7 parts by weight of the resulting product was put in a sealed tube together with 0.3 part by weight of benzoyl peroxide and heated for 6 hours at 60° C. and then for 2 hours at 120 C. for polymerization. The physical properties obtained are shown in Table 1.

EXAMPLE 2

A dental filling composite material incorporated with polyfunctional monomers was prepared.

70 parts by weight of phosphazene compound obtained in Example 1, 30 parts by weight of triethylene glycol dimethacrylate and 0.3 part by weight of benzoyl peroxide was mixed and polymerized in the same way as in Example 1. The physical properties obtained are also shown in Table 1.

EXAMPLE 3

A dental filling composite material consisting of two packages was prepared in the following way:

Package A (paste): 20 parts by weight of phosphazene compound obtained in Example 1, 2 parts by weight of triethylene glycol dimethacrylate, 0.3 part by weight of benzoyl peroxide and 0.02 part by weight of hydroquinone mono-methyl ether were mixed, with which 77.68 parts by weight of silane-treated silica powder of less than 1 μm was mixed to form a paste.

Package B (paste): 5 parts by weight of triethylene glycol dimethacrylate, 10 parts by weight of triethylol propane trimethacrylate, respectively 0.3 and 0.02 parts by weight of dimethyl-p-toluidine and hydroquinone mono-methyl ether were mixed, with which 84.68 parts by weight of silane-treated silica powder of less than 1 μm was mixed to form a paste.

Packages A and B were mixed in the ratio of 50:50 and stirred for one minute to be cured. The physical properties obtained are shown in Table 1.

Referential Example 1

A composite resin was mixed with 70 parts by weight of the conventional bisphenol-A diglycidyl dimethacrylate and 30 parts by weight of triethylene glycol dimethacrylate together with 0.3 part by weight of benzoyl peroxide and polymerized in the same way as in Example 1. The physical properties obtained are also shown in Table 1 for comparison.

Referential Example 2

Physical properties of the commercial composite resin were measured. The results are shown in Table 1.

In terms of the composition, Example 2 corresponds to referential Example 1 and Example 3 corresponds to referential Example 2, to compare the physical properties of the phosphazene compound according to the present invention with those of commercial composite resin in Table 1.

Mesurement of Physical properties (1) Polymerization shrinkage was measured by specific gravity method.

(2) Compressive strength (of specimens, $4\phi \times 5$ mm) was measured by Instron (2 mm/minute in cross head speed).

(3) Flexural strength (of specimens, $25 \times 2 \times 2$ mm) was measured in accordance with ISO 4049 (20 mm in the distance between supports, and 1 mm/minute in cross head speed).

(4) Hardness was measured by Knoop hardness tester with 100 g load.

(5) Thermal expansion coefficient (of specimens, $5\phi \times 20$ mm) was measured by the thermal expansion tester (1° C./2 minutes in the temperature-rising rate, from 30° C. to 80° C.).

(6) Water absorption was measured by immersing specimens of $9\phi \times 15$ mm in distilled water at 37° C. and determining the weight increase, expressed in % relative to the initial weight.

What is claimed is:

1. A dental cavity filling composite material comprising:

the copolymerization reaction product of a phosphazene monomer having the formula:

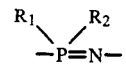

in which at least one of $R_1$ and $R_2$ is a polymerizable radical having not less than 3 carbon atoms, a copolymerizable monomer selected from the group consisting of acrylic acid, esters of acrylic acid, methacrylic acid, esters of methacrylic acid and mixtures thereof and a polyfunctional copolymerizable monomer selected from the group consisting of triethylene glycol dimethacrylate, bisphenol-A diglicydyl glycol dimethacrylate, trimethylol propane trimethacrylate, tetramethylol methane tetraacrylate and mixtures thereof.

2. A filling composite material according to claim 1, wherein the phosphazene has the formula:

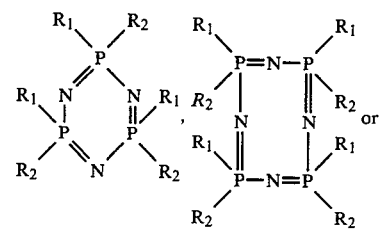

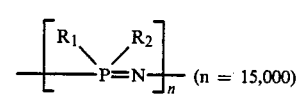

3. The filling composite material of claim 2, wherein the phosphazene has the formula:

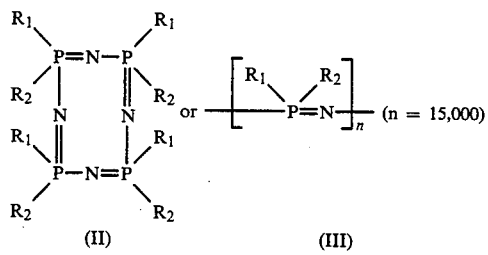

TABLE 1

| | Physical properties of the dental filling composite materials Standard Deviation in parenthesis Physical Properties | | | | | | | | | |
|---|---|---|---|---|---|---|---|---|---|---|
| Example No. | Polymerization Shrinkage (%) | | Compressive Strength (kg/cm²) | | Flexural Strength (kg/cm²) | | Hardness (Knoop) | | Thermal Expansion Coefficient ($\times 10^{-6}/°C.$) | Waters Absorption (7 days %) |
| Example 1 | 7.0 | (0.1) | 3.468 | (287) | 1.210 | (110) | 39 | (1.3) | 46.5 (3.1) | 2.01 |
| 2 | 7.4 | (0.2) | 3.710 | (152) | 1.260 | (131) | 30 | (1.9) | 56.8 (6.3) | 1.92 |
| 3 | — | — | 4.220 | (301) | 1.593 | (162) | 64 | (2.6) | 30.1 (2.4) | 0.06 |
| Referential 1 | 8.0 | (0.2) | 1.706 | (125) | 1.320 | (106) | 21 | (1.0) | 94.1 (8.1) | 2.11 |
| Example 2 | — | — | 3.480 | (274) | 1.240 | (121) | 51 | (2.1) | 41.0 (6.1) | 0.08 |

4. The filing composite material of claim 1 further comprising a filler.

* * * * *